(12) United States Patent
Ott

(10) Patent No.: US 8,204,577 B2
(45) Date of Patent: Jun. 19, 2012

(54) PROCESS AND DEVICE FOR DEEP-SELECTIVE DETECTION OF SPONTANEOUS ACTIVITIES AND GENERAL MUSCLE ACTIVITES

(76) Inventor: Lutz Ott, Fernwald-Steinbach (DE)

( * ) Notice: Subject to any disclaimer, the term of this patent is extended or adjusted under 35 U.S.C. 154(b) by 1160 days.

(21) Appl. No.: 10/592,517

(22) PCT Filed: Mar. 10, 2005

(86) PCT No.: PCT/EP2005/002532
§ 371 (c)(1),
(2), (4) Date: Sep. 8, 2006

(87) PCT Pub. No.: WO2005/087090
PCT Pub. Date: Sep. 22, 2005

(65) Prior Publication Data
US 2007/0208231 A1    Sep. 6, 2007

(30) Foreign Application Priority Data
Mar. 10, 2004  (DE) .......................... 10 2004 011 631

(51) Int. Cl.
*A61B 6/00* (2006.01)
(52) U.S. Cl. .................... 600/473; 600/436; 600/476
(58) Field of Classification Search ................... 600/473, 600/310, 322, 323, 475, 476; 250/339; 356/39, 356/41
See application file for complete search history.

(56) References Cited

U.S. PATENT DOCUMENTS

| | | | | |
|---|---|---|---|---|
| 3,900,034 A | * | 8/1975 | Katz et al. .................... | 607/89 |
| 4,930,504 A | * | 6/1990 | Diamantopoulos et al. .... | 607/88 |
| 5,353,799 A | | 10/1994 | Chance | |
| 5,779,631 A | | 7/1998 | Chance | |
| 6,198,532 B1 | * | 3/2001 | Cabib et al. ................... | 356/456 |
| 2002/0058865 A1 | * | 5/2002 | Cheng et al. .................. | 600/323 |
| 2004/0002856 A1 | | 1/2004 | Bhaskar et al. | |

FOREIGN PATENT DOCUMENTS

| | | |
|---|---|---|
| DE | 69430794 T2 | 7/1994 |
| DE | 4314835 A1 | 11/1994 |
| DE | 19640807 | 9/1997 |
| EP | 0728440 A3 | 8/1996 |
| EP | 0703445 A3 | 8/1997 |

\* cited by examiner

Primary Examiner — Tse Chen
Assistant Examiner — Joel F Brutus
(74) Attorney, Agent, or Firm — Blakely, Sokoloff, Taylor & Zafman

(57) ABSTRACT

What is described here is a process and a device for deep-selective detection of spontaneous activities and general muscle activities in biological tissue. In this process, photons of a coherent and monochromatic electromagnetic radiation of the wavelength $\lambda_1$ penetrate the tissue in the range between 600 and 1,200 nm and re-emerge from the tissue at differently distanced areas, then being detected with regard to frequency and number or intensity. By means of an evaluation program or algorithm, this information in connection with the respective area as point of emergence of the photons allows conclusions to be drawn about the muscle activity and/or number of active muscles and/or the physical position of the active muscles in the tissue. In order to improve the preciseness, it is intended to insert photons into the tissue of at least one further coherent and monochromatic electromagnetic radiation of another wavelength $\lambda_2$ and to detect them after emergence from the tissue with regard to frequency and number or intensity. The wavelengths $\lambda_1$ and $\lambda_2$ are selected in such a way that there will not occur any interference fringes.

30 Claims, 3 Drawing Sheets

Figure 1:
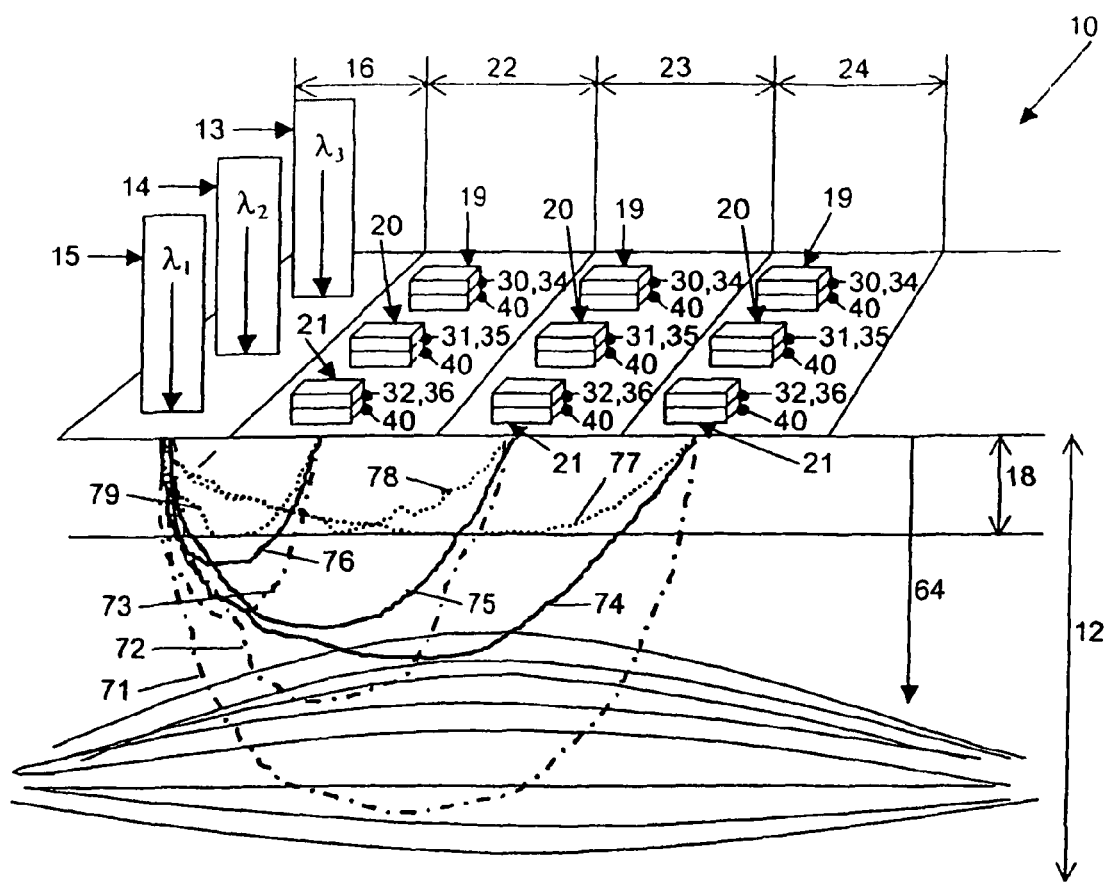

PROCESS AND DEVICE FOR DEEP-SELECTIVE DETECTION OF SPONTANEOUS ACTIVITIES AND GENERAL MUSCLE ACTIVITES

The invention concerns a process as well as a device for deep-selective detection of spontaneous activities and general muscle activities in human, animal or other biological tissue like that. The basis for this is a process in accordance with the characterizing clause of claim 1 and a device in accordance with the characterizing clause of claim 4 respectively.

A process with the features of the characterizing clause of claim 1 is well-known from EP 0 728 440 B1 whose content of disclosure in its entirety serves as subject matter of this description. This involves coherent and monochromatic electromagnetic radiation on the surface of the skin or of the tissue of the areas to be investigated by means of laser light or something like that. The photons penetrate the tissue and are scattered or absorbed depending on the optical parameter of the tissue. Since the scattering is accompanied by a change of the direction of propagation of the photons, photons are also being re-emitted from the tissue, that is they are re-scattered to the surface of the tissue or of the skin and re-emerge from the tissue. If the distance to the entrance point of the photons increases, this re-emission of the photons re-emerging from the tissue will show a decreasing intensity which usually follows an exponential curve.

A further feature of biological tissue is the fact that the light is not scattered evenly, that is isotropic, in all directions, but that a characteristic forward direction is remained in the scattering process. This is expressed by the so-called anisotropy factor G for scattering processes which has a value G of approximately 0.9 with regard to biological tissue. A value of G=0 corresponds with isotropic, a value of G=1 corresponds with pure forward scattering.

The detection of the re-emitted photons allows conclusions to be drawn about the condition of the tissue or of the muscle fibrils. Looking at photons, for example, which emerge from the tissue about 5 mm next to their entry portal, it can be assumed in all probability that these re-emerging photons have moved in a semicircular or similar curve through the tissue due to various scattering processes. Owing to the special arrangement of the measuring device and to the execution of the evaluation procedure it is certain, however, that the beginning of the curve is at the entry portal of the photons and that the end of the curve is at the measuring point of the emerging photons. Provided that these re-emerging photons actually bear any information about the movement of individual muscle fibres and/or the blood flow, it can at least be assumed that the photons re-emerging from the tissue directly next to the entry portal only bear information with regard to the muscle fibrils situated right below the surface including the movements within the blood vessels, whereas those photons emerging in a larger distance to the entry portal can also give information about deeper tissue layers. It is thus possible to obtain selective information from certain tissue depths by detecting photons re-emerging from the tissue with increasing distance to the entry portal.

As is known, the optical Doppler effect is used for the measurement of moving, scattering particles. In the course of the scattering process, light undergoes a frequency shift which increases in proportion to the speed of the moving particles. Taking the Doppler effect into consideration, it is thus possible to determine the muscle activity in tissue layers near the surface. In order to obtain an optimal Doppler signal of fibrillizing muscle fibrils in deeper tissue layers, a lightwave length of the light source, particularly of the laser, is required which is only slightly absorbed by the tissue. Wavelengths in the range of about 600 nm to 1,200 nm, preferably approximately 820 nm, are therefore useful.

It is possible to show by means of interferometric investigations that a certain amount of photons emerging from the tissue in a larger distance to the entry portal can interfere with the incident photon beam from which fact it must be concluded without a doubt that the coherence characteristics of these scattered photons are still existing. It is thus possible to detect Doppler signals with the corresponding frequency shift with regard to photons re-emerging in larger distance to the entry portal. In this process, photons with a Doppler-shifted frequency mix with such photons which have not been subject to a Doppler shift, that is with those which have only been scattered by a rigid or immovable matrix. A the point of detection on the tissue surface, this results in an intensity beat between frequency-shifted and non-frequency shifted photons, leading to a local speckle pattern the intensity of which varies with the Doppler frequency and can therefore be measured by an optical detector.

In the context of the well-known procedure and the well-known device, the evaluation of the signals is effected by two detectors recording the re-emitting photons, preferably symmetrical to the entry portal. The output signals of these detectors will be evaluated and processed appropriately in order to obtain the desired information or statement with regard to the muscle activities.

This procedure as well as the corresponding device are particularly used in the area of the "therapeutic window", that is with wavelengths in the range of 600 nm to 1,200 nm where the scattering of the irradiated photons can not be neglected. The optical absorption and scattering of light in biological tissue can be described in more detail by means of the photon transport theory. In this connection, the path of a photon that was scattered in biological tissue is being followed. At the individual local scatterers, the photon is either subject to elastic scattering or it will completely be absorbed. This makes it possible to determine the depth of penetration and the scattering process for laser light of the red waveband (600 nm) or of the infrared wavelength range (1,200 nm). Although the so-called mean free path is relatively short, light of this wavelength can deeply penetrate the tissue, since the scattering takes mainly place in forward direction (so-called Mi scattering), scattering processes occur considerably more often than absorption and absorption in the tissue is rather lower in this range of wavelength in comparison with other wavelengths. According to the transport theory, the propagation of light in the tissue is described by the following parameters: anisotropy factor, leakage coefficient, absorption coefficient, mean free path.

A synopsis of the theoretical as well as experimental investigations in accordance with the well-known procedure and the well-known device indicates that annular interference structures in a concentric position with regard to the entry portal can be obtained. With the lateral distance to the entry portal increasing, it is very likely that the photons cover larger distances in the tissue, thus also deeper penetrating the tissue. In order to be able to evaluate the information about the movement of the illuminated tissue contained in the condition of the photons, the light source should have specific characteristics such as an adequate coherence length, for example. It should also be monochromatic and operational in single-mode condition.

A sufficiently high coherence length is required for obtaining the desired information, so that an interference pattern can be achieved on the surface of the device. The development of the interference pattern is based on the assumption that photons which are scattered close to the surface of the tissue or of the skin do not undergo a change in frequency and that these so to speak non-scattered photons interfere with such photons which are scattered in the depth on moving particles, that is on muscle fibrils, thus undergoing a frequency shift. The frequency-shifted scattered light which was scattered on moving particles is made congruent on the detector surface with original light, resulting in a beat frequency or an interference pattern. In order to obtain these beat frequencies from deeper tissue layers, a wavelength in the range of 600 nm to approx. 1,200 nm is required and it has also to be ensured that the light source has a sufficient coherence length. Typical interference patterns are also provable for deep tissue layers where the information will be obtained from an increasing depth of the tissue if the distance between the detector surface and the entry portal increases. This can be proven for large lateral distances between the detector surface and the entry portal in a range of approx. 15 mm to 30 mm.

This well-known process and well known device respectively have the disadvantage that only one light source with coherent monochromatic light is being used. This leads to a situation where the detectors arranged in some distance to the light source in order to record the photons emerging from the tissue will detect a mixture of photons coming from the layers near the surface, from the deeper layers of the tissue as well as from muscle activities. This results in a falsification of the measured values which in the extreme case may lead to a situation where it is not possible to make an exact statement on the detected photons of a certain depth since 50% of the photons measured by the detector come from layers near the surface of the tissue and 50% come from deeper layers of the tissue. An exact statement on deep-selective muscle activities in the tissue to be investigated can therefore not clearly be made.

The investigation is thus based on the task to provide a process or a device of the kind mentioned at the beginning which is considerably improved with regard to deep-selective detection of spontaneous activities and general muscle activities in human, animal or other biological tissue like that.

As regards the process, this task is solved by inserting photons into the tissue which are of a coherent and monochromatic electromagnetic radiation of at least another wavelength $\lambda_2$ and detecting them after emerging from the tissue with regard to frequency and number or intensity, with the wavelengths $\lambda_1$ and $\lambda_2$ being selected in such a way that interference fringes will not occur.

The invention makes use of the fact that monochromatic light with a shorter wavelength such as green light with a wavelength in the range of 532 nm, for example, is immediately absorbed in the deeper areas of the tissue. The photons coming from this light source which are scattered back to the tissue surface and detected afterwards therefore exclusively reflect the blood flow at the surface of the tissue and in the areas near the surface. The second monochromatic light source, however, has a larger wave length, for example in the infrared range of approx. 780 to 1,000 nm. This light goes considerably deeper into the biological tissue. The photons of this wavelength range with the corresponding shift in frequency which have been scattered back and detected after emerging from the surface come from the entire tissue up to the depth where a complete absorption takes place, and particularly from the layers near the surface, as well. For these detected photons, a differential reflection can however be carried out, based on the detected photons of the light source with monochromatic light of the shorter wavelength, for example the aforementioned wavelength of 532 nm (green). Information from the deeper layers alone is thus obtained, that is after evaluation only the spontaneous activity or the muscle activity in deeper regions of the tissue. This altogether renders a much clearer picture of the muscle activity in the tissue.

The re-emitted photons of the light with a shorter wavelength give information about the blood flow in the surface or in the layers near the surface of the biological tissue, whereas the differential reflection of the re-emitted photons of both wavelengths gives information about the spontaneous and muscle activity in deeper layers of the tissue.

After a first advantageous embodiment of the invention, it is intended to carry out the detection of spontaneous activities or general muscle activities in a non-invasive way. For this purpose, the electromagnetic radiation in the body is simply inserted into the tissue to be investigated, similar to an arthroscopic procedure, for example by means of a light-conducting fibre, and will be detected after backscattering and emergence from the tissue.

With regard to certain investigations it is particularly advantageous to carry out the detection of spontaneous activities or general muscle activities invasively. In this case, a light-conducting fibre is for example inserted into the tissue, similar to an arthroscopic procedure, and is carried up to the tissue to be investigated where it is placed appropriately in order to carry out the detection.

According to another advantageous embodiment of the process in accordance with the present invention, photons of another coherent and unchromatic electromagnetic radiation of the wavelength $\lambda_3$ are being inserted into the tissue and detected with regard to frequency and number or intensity after emergence from the tissue. For this purpose, the wavelength $\lambda_3$ is smaller than 600 nm, so that interference fringes will not occur between the frequency-shifted photons of the different wavelengths $\lambda_1, \lambda_2$ und $\lambda_3$ which have been scattered on the tissue. Owing to this measure, the preciseness of the deep-selective detection of spontaneous or muscle activity in the tissue is further increased, since now there are three different types of photons penetrating the tissue which will completely be absorbed there in different layers. With the help of the back-scattered and frequency-shifted photons of the different wavelengths $\lambda_1$, $\lambda_2$ and $\lambda_3$ as well as of the previously described differential measuring it is possible to carry out an even more precise depth profiling of the spontaneous and muscle activity.

According to another advantageous embodiment of the process in accordance with the present invention, the photons re-emerging from the tissue will be detected and recorded with regard to frequency and number or intensity in dependency on the distance to their entrance point. Owing to this measure, the spontaneous and muscle activity is not only detected on one spot, but on several spots at different distances to the entrance point. This ensures an even more precise deep-selective detection subject to the distance from the entrance point of the photons in the whole area around the entrance point.

As regards the device, this task is solved by means of a device with the features of claim 6. This provides for at least one further radiation source for sending out photons into the tissue, the photons being of a coherent and monochromatic electromagnetic radiation of a wavelength of $\lambda_2 \neq \lambda_1$, with the detectors also recording the frequency-shifted photons of wavelength $\lambda_2$ which have been scattered on the tissue with regard to frequency and number or intensity, making use of them for deep-selective recording of the spontaneous and muscle activities respectively. In accordance with the present invention, another light source is thus used which radiates photons of a coherent and monochromatic electromagnetic radiation with $\lambda_2 \neq \lambda_1$ into the tissue. In the course of this, the photons of the different coherent and monochromatic electromagnetic radiation of the wavelengths $\lambda_1$ and $\lambda_2$ go into different depths of the tissue before they are completely absorbed. This means that the photons with the lower wavelength are already completely absorbed in layers which are closer to the surface, whereas the photons of the radiation with a longer wavelength deeper penetrate into the tissue. This facilitates a more precise deep-selective detection of the spontaneous and muscle activity.

After an advantageous embodiment of the invention, devices are scheduled for an invasive detection of the spontaneous activity or of the muscle activity. This could be light-conducting fibres, for example, which are being inserted into the body as it is done in an arthroscopic procedure. Through these devices, the electromagnetic radiation is directly applied to the area in the body where the detection of the spontaneous and muscle activity is to take place. In order to be able to detect the back-scattered photons, these devices are provided with a sensor such as a photodiode, for example.

After the back-scattered photons have been detected by the photodiode, the electromagnetic radiation will be transmitted to evaluation electronics.

Alternatively, it is also possible to provide devices for non-invasive detection of the spontaneous activity or of the general muscle activity. In this case the device is simply put on the surface of the tissue, for example on the skin, by using a case, for example. It is again possible to carry out the detection of the back-scattered photons by using photodiodes, with the detected electromagnetic radiation also being transmitted to evaluation electronics.

After an advantageous embodiment of the invention it is intended to send out another radiation source for sending out photons of a coherent and monochromatic electromagnetic radiation of the wavelength $\lambda_3$ into the tissue, with $\lambda_3 \neq \lambda_2 \neq \lambda_1$. This measure facilitates a direct detection of the scattered and frequency-shifted photons with different wavelengths $\lambda_1$, $\lambda_2$ and $\lambda_3$ after emergence from the tissue, thus allowing an even more precise deep-selective detection of spontaneous and muscle activity. It is therefore possible to prepare a detailed depth profile of the spontaneous and muscle activity respectively.

In order to ensure a precise detection both in the surface or the layers near the surface of the tissue as well as in deeper layers and in the muscles lying underneath, the invention determines that the wavelength $\lambda_1$ shall be in the range between 600 nm and 700 nm, the wavelength $\lambda_2$ in the range between 700 nm and 1,200 nm and the wavelength $\lambda_3$ below 600 nm. The photons of the wavelength $\lambda_3$ are already completely absorbed by the tissue in low depth of the surface or in the layers near the surface. The photons which are being back-scattered are caused by scattering processes near the surface of the tissue and emerge from the tissue close to the entrance point. The photons of the light of the wavelength $\lambda_1$, however, go into the deeper areas of the tissue before a complete absorption takes place. Photons of this wavelength that are scattered back to the surface therefore come from all layers of the tissue where a complete absorption has not yet taken place. These photons also emerge from the tissue rather close to the entrance point. Owing to its deeper depth of penetration, the majority of the back-scattered photons are found in an area around the entrance point which is further away from the latter than the point of emergence of the photons with a lower wavelength. The photons of the coherent monochromatic electromagnetic radiation of the wavelength $\lambda_2$ in the range of 700 nm and 1,200 nm can penetrate the tissue most deeply because of their higher energy. Complete absorption takes place even deeper in the tissue than it is the case with the electromagnetic radiation of the wavelength $\lambda_1$. The photons which are scattered back to the surface beforehand therefore emerge from the tissue surface in an even larger distance to the entrance point than the photons of the electromagnetic radiation of the wavelength $\lambda_1$. There are nevertheless still overlapping areas where photons of the electromagnetic radiation of the different wavelengths $\lambda_1$, $\lambda_2$, $\lambda_3$ can be detected at the surface. But since the intensity of the back-scattered photons exponentially decreases subject to the distance to the entrance point, it is possible to obtain very precise depths profiles of the spontaneous and muscle activity by means of difference reflection with regard to the various frequencies and intensities of the back-scattered and frequency-shifted photons.

In order to ensure that the design of the device is as compact as possible it is intended to realize at least one of the radiation sources as semiconductor laser.

The realization of at least one of the radiation sources as laser diode aims at the same direction.

According to a particularly advantageous embodiment of the invention it is intended that a separate detector will be allocated to each area for each of the wavelengths $\lambda_1$, $\lambda_2$ and $\lambda_3$. Due to this measure, the back-scattered and frequency-shifted photons of the electromagnetic radiation of the different wavelengths $\lambda_1$, $\lambda_2$ and $\lambda_3$ will be recorded by a separate detector each, so that a strict separation of these wavelength ranges is effected in the course of detection and a misdetection is being ruled out.

This could have the advantage that each detector is provided with one or several sensors for detecting one of the wavelengths $\lambda_1$, $\lambda_2$ or $\lambda_3$. These sensors can for example be realized as photodiode or as optical filter. If each detector is provided with two sensors, then their difference signal may be used for the reduction and minimization of the noise and be reinforced accordingly.

According to another particularly advantageous embodiment of the invention, a common detector is allocated to each area for all wavelengths $\lambda_1$, $\lambda_2$ and $\lambda_3$. Due to this measure, it is achieved that the whole device, particularly in the area of the detector, is kept very small, since one detector is sufficient in order to detect all necessary wavelengths.

It is particularly advantageous if the common detector has different sensors for each of the wavelengths $\lambda_1$, $\lambda_2$ and $\lambda_3$.

These sensors may for example be realized as photodiodes or optical filters, each of them for one of the wavelengths $\lambda_1$, $\lambda_2$ or $\lambda_3$. Due to this measure, it is not necessary to use several detector units, resulting not only in a very small construction, but also in saving of costs and raw materials.

Since the frequency-shifted photons of the electromagnetic radiation with the shortest wavelength $\lambda_3$ which are scattered back to the tissue surface almost exclusively re-emerge from the tissue rather close to the entrance point of the photons, it is intended to place the corresponding detectors for the shortest wavelength $\lambda_3$ only close to the entrance point of the photons. This again contributes to an even more compact and cost-effective construction.

Since very close to the entry portal, it is only the emerging photons of the wavelength $\lambda_3$ which contain unambiguous information about the blood flow, back-scattered photons of the wavelengths $\lambda_3$ and $\lambda_2$ will be cut out, for example by optical means such as optical filters, for example.

Alternatively or additionally it is possible, of course, not to place any of those detectors responding to the wavelengths $\lambda_1$ and $\lambda_2$ in the area close to the point of emergence.

According to an advantageous embodiment of the invention it is intended to allocate a compensating circuit to each photodiode minimizing an offset in the output signal of the photodiode. If an offset voltage is applied to the photodiode, a so-called dark current flows through the resistance inherent in the photodiode. On amplification, this dark current leads to an unwelcome offset in the output signal. The output signal also contains the signals of the photons scattered back in the tissue which serve for the detection of spontaneous activities and general muscle activities. By superposing the frequency-shifted scattered light on the detector surface with the original light that is not frequency-shifted or by making them congruent, a beat frequency or interference pattern is caused. Apart from the signal values, this scattered light also contains the noise components of the laser light source (mode interference, frequency and amplitude noise) which are filtered out in this detection by means of a broadband filter, for example. The share of direct-current voltage of the beat frequency of the scattered light is minimized by a trimmer potentiometer. This improves the signal-noise ratio. Furthermore, the compensating circuit makes it possible to keep the offset of the photodiode and the share of direct-current voltage of the signal as low as possible, so that basically only the actual signals are being detected. In contrast to a differential amplifier, this type of detection facilitates a detector of compact design. Alternatively it is also possible, of course, to minimize the share of direct-current voltage of the detected photons additionally or only with the help of an algorithm.

According to another advantageous aspect of the invention, the light sources as well as the detectors and electronic components such as preamplifier, if necessary, differential amplifier and analogue-to-digital converter, if necessary, are together arranged in a sensing head which can flatly be placed on the tissue or on the skin and can only be connected with an evaluation unit, particularly with a processor, by means of electric conductors. Except for the processor, the whole device is thus fastened to a single carrier plate or a printed circuit board or something like that which is included in a closed, physiologically harmless and shielded case. This case can also be constructed in such a way that it may be placed invasively within the body of the tissue to be investigated, similar to an arthroscopic procedure.

Glass or plastic platelets shall be used for the flat fastening on the tissue or the skin which have the advantage that they let pass the photons of the electromagnetic radiation of the given wavelengths $\lambda_1$, $\lambda_2$ and $\lambda_3$.

In order to realize a particularly compact case for the device it is intended to arrange the detectors in a distance of up to 40 mm from the radiation sources. This area mainly depends on the wavelengths used and the absorption coefficients by which they are accompanied as well as on the coherence length of the light sources used.

Further targets, advantages, features and possible applications of the present invention result from the following description of embodiments on the basis of drawings. All of the features described and/or presented by illustration constitute by themselves or in any sensible combination the subject-matter of the present invention irrespective of their integration in the claims and of how these relate back.

Figure 2:
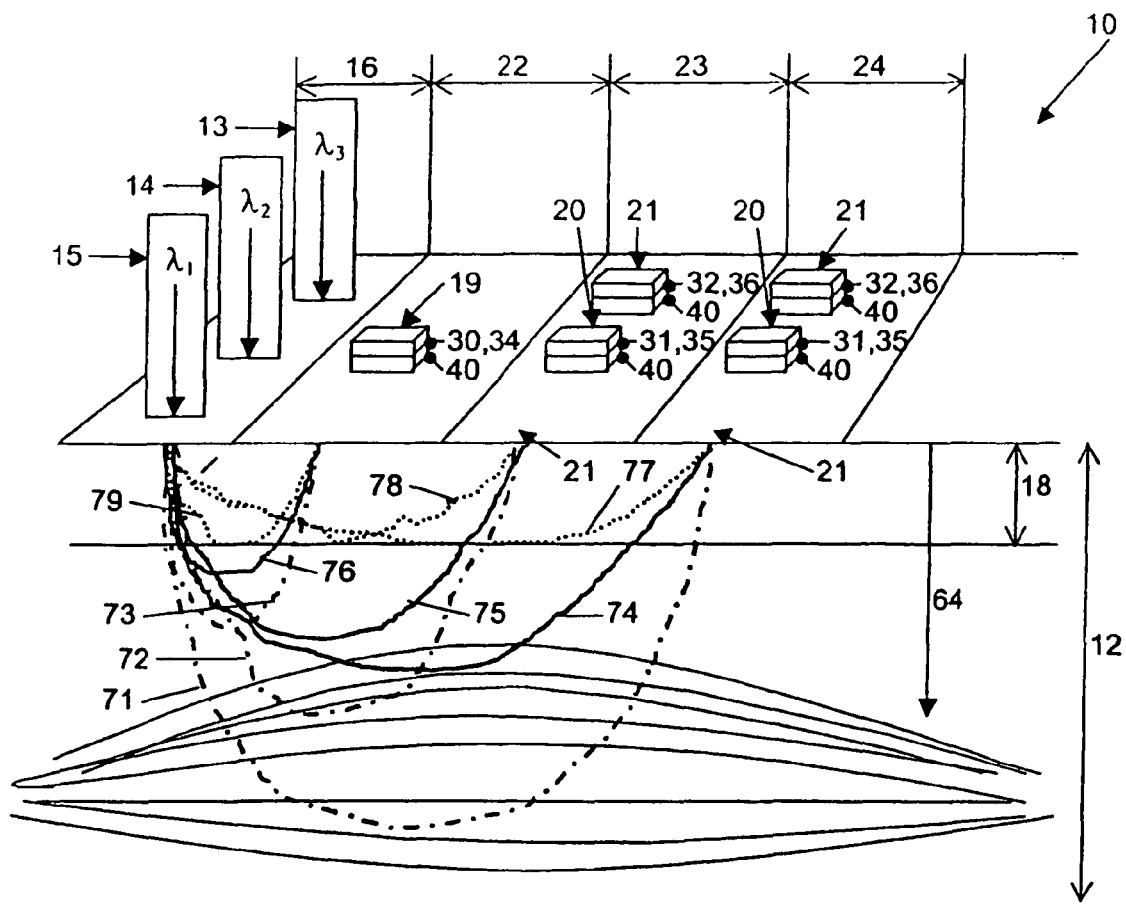
Figure 3:
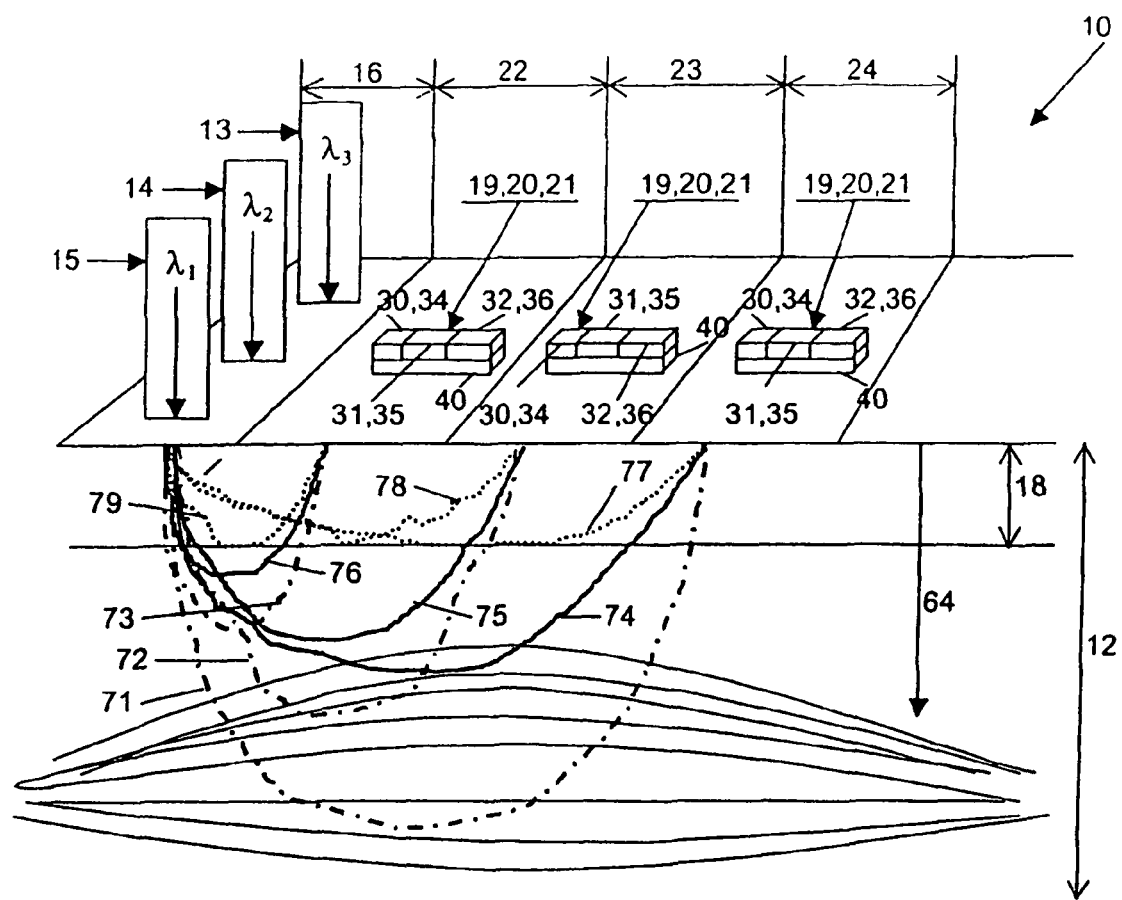

The following is shown:

FIG. 1 a schematic illustration of a first embodiment of the device fastened on tissue in accordance with the present invention, FIG. 2 a second embodiment of the device in accordance with the present invention in a perspective illustration, FIG. 3 a third embodiment of the device in accordance with the present invention in a perspective illustration.

The device 10 presented in the FIGS. 1 to 3 for the measurement of spontaneous and muscle activities in human, animal or other biological tissue like that 12 shows three light sources 13, 14 and 15, particularly three semiconductor lasers, for sending out photons into the tissue 12.

The device 10 is fastened to the tissue 12 or the skin 18 of the tissue by means of a carrier plate, with photons penetrating the skin 18 or the total tissue 12 through a first area 16 which in the main is locally well-defined. Some of the photons are being scattered in the tissue 12 including the skin 18, and some of them are being absorbed, with some of the possible distances covered by the photons 71 to 79 are presented in the figures by means of illustrations as well as schematically. It can clearly be seen that with a growing depth of penetration 64, the photons re-emerge from the tissue 12 and from the skin 18 at an increasingly greater distance to the first area 16.

Furthermore, the device 10 is provided with several detectors 19, 20, 21 for recording photons emerging from the further areas 22, 23 and 24 of the skin 18 or of the tissue 12. The further areas 22, 23 und 24 are arranged in different distances from the first area 16.

Each of the detectors 19, 20 and 21 is provided with a glass or plastic platelet 40 which can flatly be put on the tissue 12 or the skin 18, and behind each of which is put a photodiode 30, 31, 32 and/or an optical filter 34, 35, 36 as sensor.

A glass or plastic platelet for being flatly put on the tissue 12 or the skin 18 can also be allocated to the light sources 13, 14, 15. It is also possible to put in polarizing filters behind the light sources 13, 14, 15 and in front of the detectors 19, 20, 21. In place of the glass or plastic platelets, it is also possible to use a piece of a light-conducting fibre or collimation optics for focussing the laser light on the tissue 12 or on the skin 18.

The wavelength $\lambda_1$ of the radiation source 14 is in the range of approximately 600 nm to about 700 nm, preferably about 633 nm, the wavelength $\lambda_2$ of the electromagnetic radiation coming from the radiation source 15 is in the range of approximately 700 nm to about 1,200 nm, preferably about 780 nm, whereas the wavelength $\lambda_3$ of the electromagnetic radiation sent out by the radiation source 13 is somewhere below 600 nm, preferably about 532 nm.

In the embodiment according to FIG. 1, a separate detector 19, 20, 21 is allocated to each of the further areas 22, 23, 24 for the detection of the back-scattered, frequency-shifted photons of the original wavelengths $\lambda_1$, $\lambda_2$, $\lambda_3$ of the different electromagnetic radiations of the radiation sources 13, 14, 15. There is exactly one detector 19, 20, 21 for each wavelength $\lambda_1$, $\lambda_2$, $\lambda_3$ in each area 22, 23, 24. In the embodiment, the distances between the individual detectors 19, 20 and 21 are equidistant. It goes without saying that it is also possible to choose other distances of the individual detectors 19, 20 and 21 with regard to the first area 16; this is determined by the special requirements of the respective system. The further areas 22, 23, 24 and the respective corresponding detectors 19, 20, 21 are arranged up to a maximum distance of about 40 mm from the first area 16.

Since the photodiodes 30, 31, 32 have an internal resistance which generates a so-called dark current if applying a voltage, the offset caused by this in the output signal of the photodiodes 30, 31, 32 is minimized by a compensating circuit (not shown).

Owing to this compensating circuit, the share of the direct-current voltage of the detected back-scattered photons on which the actual frequency-shifted potential is situated can be zeroized by means of a trimmer potentiometer, for example. The direct-current voltage share of the detected photons can be aligned to zero through this trimmer potentiometer. In case of a following amplification by means of an operational amplifier, for example, it is only the actual frequency-shifted signal that will be amplified.

Alternatively, it is of course also possible to reduce the direct-current voltage share of the detected photons additionally or only with the help of an algorithm.

In contrast to the embodiment according to FIG. 1, the embodiments according to the FIGS. 2 and 3 do not provide for an individual detector for each wavelength $\lambda_1$, $\lambda_2$, $\lambda_3$ in each area 22, 23, 24.

According to FIG. 2, a detector 19 for the shortest wavelength $\lambda_3$ is only arranged rather close to the area 22. With regard to the areas 23, 24, it is not necessary to provide them with further detectors 19 for the wavelength $\lambda_3$, since in these areas, the possibility of detecting re-emitted frequency-shifted photons of the electromagnetic radiation with the wavelength $\lambda_3$ is virtually non-existent, since the intensity of the signal decreases exponentially with the distance to the entrance point 16. Since the photons of the electromagnetic radiation of the wavelength $\lambda_3$ only have a very small depth of penetration 64 into the tissue 12, which usually does not exceed the thickness of the skin 18, and since the back-scattered photons mainly move on circular or elliptical orbits, the curves 79 of the back-scattered photons of the electromagnetic radiation of the wavelength $\lambda_3$ occur many times more often than the curves 78 und 77, because of the exponential decrease of the intensity. The photons on the curves 77 and 78 can therefore completely be ignored.

Owing to the fact that the photons of the electromagnetic radiation of the wavelengths $\lambda_1$ and $\lambda_2$ shall mainly reflect the spontaneous and muscle activity in the deeper layers of the tissue 12, according to the embodiment as shown in FIG. 2, it is not intended to arrange any detectors in the area 22 for the wavelengths $\lambda_1$ and $\lambda_2$.

The embodiment according to FIG. 3 provides for one detector 19, 20, 21 in each area 22, 23, 24 which will be able to record photons of the electromagnetic radiation of all three wavelengths $\lambda_1$, $\lambda_2$ and $\lambda_3$. For this purpose, sensors in the form of photodiodes 30, 31, 32 and/or optical filters 34, 35, 36 are arranged in each detector 19, 20, 21. By using only one detector 19, 20, 21 for the area 22, 23, 24, the device 10 is kept very small. All of the parts required for detecting each of the wavelengths $\lambda_1$, $\lambda_2$, $\lambda_3$ are put in only one single detector 19, 20, 21.

With regard to all of the embodiments described above, it is intended to arrange the device 10 with the exception of a non-represented processor, that is the radiation sources 13, 14, 15, the detectors 19, 20, 21 and the non-represented electronic components, such as preamplifier, if necessary, differential amplifier and analogue-to-digital converter, together in a sensing head which can flatly be placed on the tissue or on the skin. The sensing head is only connected with the evaluation unit, particularly with the processor, by means of electric conductors. The inside of the sensing head can be filled with filling material.

Especially for invasive measurements, it is sensible, however, to provide the sensing head only with the sensors and/or detectors 19, 20, 21, because of the compact design that can thus be achieved. The detected signals will be transmitted to the evaluation electronics that are arranged in a non-invasive way.

LIST OF REFERENCE MARKS

10 Device
12 Tissue
13 Light Source
14 Light Source
15 Light Source
16 First Area
18 Skin
19 Detector
20 Detector
21 Detector
22 Area
23 Area
24 Area
30 Photodiode
31 Photodiode
32 Photodiode
34 Optical Filter
35 Optical Filter
36 Optical Filter
40 Plastic Platelet
64 Depth of Penetration
71-79 Possible distances covered by the photons

The invention claimed is:

1. A process for deep selective detection of spontaneous activities and general muscle activities in tissue comprising:
   emitting photons of a coherent and monochromatic electromagnetic radiation of a wavelength $\lambda_1$ in a range between 600 nm and 1200 nm such that the emitted photons penetrate the tissue through a first area in the tissue;
   emitting photons of a coherent and monochromatic electromagnetic radiation of a wavelength $\lambda_2$ in a range between 600 nm and 1200 nm such that the emitted photons penetrate the tissue through a second area in the tissue, wherein the wavelengths $\lambda_1$ and $\lambda_2$ are selected such that interference fringes do not occur;
   detecting the photons of the wavelength $\lambda_1$ as they re emerge from the tissue in a third area of the tissue that is separate from the first area, wherein the photons are detected with regard to a first frequency shift and a first number or intensity of photons by means of an evaluation program or algorithm;
   detecting the photons of the wavelength $\lambda_2$ as they re-emerge from the tissue in a fourth area of the tissue that is separate from the second area, wherein the photons are detected with regard to a second frequency shift and second number or intensity of photons by means of an evaluation program or algorithm;
   determining based on the first and second frequency shifts, the first and second number or intensity of photons, and the location of the second area in relation to the third area and the location of the second area in relation to the fourth area muscle activity, a number of active muscles, and a physical position for each of the active muscles in the tissue;
   a process for deep-selective detection of spontaneous activities and general muscle activities in tissue that utilizes an optical Doppler effect.
   wherein the first and second detected frequencies are both Doppler-shifted such that the re-emerging photons are detected with respect to a first Doppler-shifted frequency or with respect to a second Doppler-shifted frequency.

2. The process according to claim 1, wherein the detection of photons and the determination of muscle activities is non-invasive.

3. The process according to claim 1, wherein the detection of photons and the determination of muscle activities is invasive.

4. The process according to one of the aforementioned claims, further comprising:
   emitting photons of a coherent and monochromatic electromagnetic radiation of a wavelength $\lambda_3$ which is less than 600 nm and 1200 nm such that the emitted photons penetrate the tissue through a fifth area in the tissue, wherein the wavelengths $\lambda_1$, $\lambda_2$ and $\lambda_3$ are selected and has been inserted such that interference fringes do not occur and has been inserted;
   detecting the photons of the wavelength $\lambda_3$ as they re-emerge from the tissue in a sixth area of the tissue that is separate from the fifth area, wherein the photons are detected with regard to a third frequency shift and a third number or intensity of photons by means of an evaluation program or algorithm.

5. The process according to one of claims 1 to 3, further comprising:
   recording the first and second frequency shift, the first and second number or intensity of photons, and locations of the first, second, third and fourth areas of the tissue.

6. A device for deep selective detection of spontaneous activities and general muscle activities in tissue, comprising:
   a first radiation source for emitting photons of a coherent and monochromatic electromagnetic radiation of a wavelength $\lambda 1$ (600 nm $\leq \lambda_1 \leq$ 1200 nm through a locally defined first area of the tissue;
   a plurality of detectors for detecting and recording the photons re-emerging from the tissue at a set of areas of the tissue, the set areas are arranged at different distances from the first area, wherein the emerging photons are detected by the plurality of detectors with regard to a first frequency shift and a first number or intensity of photons using a detected interference pattern based on the photons emerging from the set of areas, a distance from the first area to an area of the set of areas that each photon emerges from the tissue t in connection with the frequency-shifted photons scattered on the tissue, wherein a deep-selective recording of muscle activity in the tissue is carried out based on the detected frequency shifts,
   at least one further radiation source which emits photons of a coherent and monochromatic electromagnetic radiation of a wavelength $\lambda_2$ into the tissue, wherein $\lambda_2 \neq \lambda_1$;
a plurality of additional detectors which also record the frequency-shifted photons scattered on the tissue of the original wavelength $\lambda_1$ with regard to frequency shifts and number or intensity of photons for deep-selective recording of muscle activity; and
   a process for deep-selective detection of spontaneous activities and general muscle activities in tissue that utilizes an optical Doppler effect,
   wherein the first and second detected frequencies are both Doppler-shifted such that the re-emerging photons are detected with respect to a first Doppler-shifted frequency or with respect to a second Doppler-shifted frequency.

7. The device according to claim 6, wherein the device is intended to use a light-conducting fibre for the invasive detection of spontaneous activity or muscle activity.

8. The device according to claim 6, wherein the device is intended to use means for the non invasive detection of spontaneous activity or muscle activity.

9. The device according to claim 6, further comprising:
   another radiation source for sending out photons of a coherent and monochromatic electromagnetic radiation of a wavelength $\lambda_3$ into the tissue, wherein $\lambda_3 \neq \lambda_2 \neq \lambda_1$.

10. The device according to claim 9, wherein 600 nm $\leq \lambda_2 \leq$ 1200 nm and $\lambda_3 \leq$ 600 nm.

11. The device according to claim 9, wherein 600 nm $\leq \lambda_1 \leq$ 700 nm, 700 nm $\leq \lambda_2 \leq$ 1200 nm and $\lambda_3 \leq$ 600 nm.

12. The device according to claim 9, wherein a separate detector is allocated to each area for each wavelength $\lambda_1$, $\lambda_2$, $\lambda_3$.

13. The device according to claim 12, wherein each detector is provided with one or several sensors for the detection of one of the wavelengths $\lambda_1$, $\lambda_2$, $\lambda_3$.

14. The device according to claim 13, wherein the sensor is realized as a photodiode.

15. The device according to claim 14, wherein a compensating circuit is allocated to each photodiode minimizing an offset in an output signal of the photodiode as well as an occurring duvet current voltage share of the detected photons.

16. The device according to claim 15, wherein the direct current voltage share of the detected photons is minimized by a filter and/or an algorithm.

17. The device according to claim 13, wherein the sensor is realized as an optical filler.

18. The device according to claim 9, wherein a common detector for all wavelengths $\lambda_1$, $\lambda_2$, $\lambda_3$ is allocated to each the second area and the set of areas.

19. The device according to claim 18, wherein the common detector is provided with different sensors for each of the wavelengths $\lambda_1$, $\lambda_2$, $\lambda_3$.

20. The device according to claim 19, wherein each of the sensors is realized as an optical filter for one of the wavelengths $\lambda_1$, $\lambda_2$, $\lambda_3$.

21. The device according to claim 20, wherein each of the sensors is realized as an optical filter for one of the wavelengths $\lambda_1$, $\lambda_2$, $\lambda_3$.

22. The device according to claim 9, wherein the detectors for the shortest wavelength $\lambda_3$ are only arranged close to the entrance point of the photons.

23. The device according to one of the claims 6 to 11, wherein at least one of the radiation sources is realized as a semiconductor laser.

24. The device according to one of the claims 6 to 11, wherein at least one of the radiation sources is realized as a laser diode.

25. The device according to claim 6, wherein the radiation sources as well as the detectors and electronic components are together arranged in a sensing head which can be flatly placed on the tissue or on skin and can be connected with an evaluation unit, particularly with a processor, by means of electric conductors.

26. The device according to claim 6, wherein the detector for invasive detection can be inserted into the body of the tissue to be investigated.

27. The device according to claim 25 or 26, wherein glass or plastic platelets are used for placing the sensing head flatly on the tissue or on the skin.

28. The device according to claim 6, wherein the detectors are arranged at a distance of 15 mm to 30 mm from the radiation sources.

29. A process for deep-selective detection of spontaneous activities and general muscle activities in tissue comprising:
   emitting photons of a coherent and monochromatic electromagnetic radiation of a wavelength $\lambda_1$ in a range of a wavelength of green light such that the emitted photons penetrate the tissue through a first area in the tissue;
   emitting photons of a coherent and monochromatic electromagnetic radiation of a wavelength $\lambda_2$ in a range between 780 nm and 1000 nm such that the emitted photons penetrate the tissue through a second area in the tissue, wherein the wavelengths $\lambda_1$ and $\lambda_2$ are selected such that interference fringes do not occur;

detecting the photons of the wavelength $\lambda_1$ as they re-emerge from the tissue in a third area of the tissue that is separate from the first area, wherein the photons are detected with regard to a first frequency shift and a first number or intensity of photons by means of an evaluation program or algorithm;

detecting the photons of the wavelength $\lambda_2$ as they re-emerge from the tissue in a fourth area of the tissue that is separate from the second area, wherein the photons are detected with regard to a second frequency shift and second number or intensity of photons by means of an evaluation program or algorithm;

determining based on the first and second frequency shifts, the first and second number or intensity of photons, and the location of the second area in relation to the third area and the location of the second area in relation to the fourth area muscle activity, a number of active muscles, and a physical position for each of the active muscles in the tissue; and a process for deep-selective detection of spontaneous activities and general muscle activities in tissue that utilizes an optical Doppler effect.

wherein the first and second detected frequencies are both Doppler-shifted such that the re-emerging photons are detected with respect to a first Doppler-shifted frequency or with respect to a second Doppler-shifted frequency.

30. A device for deep-selective detection of spontaneous activities and general muscle activities in tissue, comprising:

a first radiation source for emitting photons of a coherent and monochromatic electromagnetic radiation of a wavelength $\lambda 1$ (600 nm$\leq\lambda_1\leq$1200 nm) through a locally defined first area of the tissue;

a plurality of detectors for detecting and recording the photons re-emerging from the tissue at a set of areas of the tissue, the set areas are arranged at different distances from the first area, wherein the emerging photons are detected by the plurality of detectors with regard to a first frequency shift and a first number or intensity of photons using a detected interference pattern based on the photons emerging from the set of areas, a distance from the first area to an area of the set of areas that each photon emerges from the tissue t in connection with the frequency-shifted photons scattered on the tissue, wherein a deep-selective recording of muscle activity in the tissue is carried out based on the detected frequency shifts;

at least one further radiation source which emits photons of a coherent and monochromatic electromagnetic radiation of a wavelength $\lambda_2$ into the tissue, wherein $\lambda_2 \neq \lambda_1$;

a plurality of additional detectors which also record the frequency-shifted photons scattered on the tissue of the original wavelength $\lambda_1$ with regard to frequency shifts and number or intensity of photons for deep-selective recording of muscle activity, wherein the wavelength $\lambda_1$ is in the range of a wavelength of green fight and the wavelength $\lambda_2$ is in the range between 780 nm and 1000 nm; and a process for deep-selective detection of spontaneous activities and general muscle activities in tissue that utilizes an optical Doppler effect, wherein the first and second detected frequencies are both Doppler-shifted such that the re-emerging photons are detected with respect to a first Doppler-shifted frequency or with respect to a second Doppler-shifted frequency.

* * * * *

UNITED STATES PATENT AND TRADEMARK OFFICE
CERTIFICATE OF CORRECTION

PATENT NO. : 8,204,577 B2
APPLICATION NO. : 10/592517
DATED : June 19, 2012
INVENTOR(S) : Lutz Ott Page 1 of 1

It is certified that error appears in the above-identified patent and that said Letters Patent is hereby corrected as shown below:

In the Claims, Column 11, Claim 6, Line 26, please delete "nm through" and insert -- nm) through --.

Column 11, Claim 8, Line 62, please delete "non invasibe" and insert -- non-invasive --.

Column 12, Claim 15, Line 16, please delete "duvet current" and insert -- direct-current --.

Column 12, Claim 17, Line 21, please delete "filler" and insert -- filter --.

Column 12, Claim 20, Line 29, please delete "an optical filter" and insert -- a photodiode --.

Column 12, Claim 26, Line 49, please delete "detector" and insert -- detectors --.

Column 14, Claim 30, Line 23, please delete "fight" and insert -- light --.

Signed and Sealed this
Eighteenth Day of September, 2012

David J. Kappos
*Director of the United States Patent and Trademark Office*